(12) United States Patent  
Rosenthal et al.

(10) Patent No.: US 7,291,165 B2  
(45) Date of Patent: Nov. 6, 2007

(54) MEDICAL DEVICE FOR DELIVERING BIOLOGICALLY ACTIVE MATERIAL

(75) Inventors: Arthur L. Rosenthal, Boston, MA (US); William Joseph Shaw, Cambridge, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 10/062,794

(22) Filed: Jan. 31, 2002

(65) Prior Publication Data

US 2003/0144727 A1    Jul. 31, 2003

(51) Int. Cl.  
*A61F 2/06* (2006.01)

(52) U.S. Cl. ..................................... 623/1.15

(58) Field of Classification Search ...... 623/1.11–1.48, 623/1.32  
See application file for complete search history.

(56) References Cited

U.S. PATENT DOCUMENTS

| | | | |
|---|---|---|---|
| 4,728,328 A | 3/1988 | Hughes et al. | |
| 5,064,435 A | 11/1991 | Poter | |
| 5,609,629 A * | 3/1997 | Fearnot et al. | 623/1.42 |
| 5,643,309 A * | 7/1997 | Myler et al. | 623/1.15 |
| 5,667,523 A | 9/1997 | Bynon et al. | |
| 5,693,085 A | 12/1997 | Buirge et al. | |
| 5,725,572 A | 3/1998 | Lam et al. | |
| 5,746,691 A | 5/1998 | Frantzen | |
| 5,817,126 A | 10/1998 | Imran | |
| 5,824,045 A | 10/1998 | Alt | |
| 5,824,049 A | 10/1998 | Ragheb et al. | |
| 5,843,172 A | 12/1998 | Yan | |
| 6,004,346 A | 12/1999 | Wolf et al. | |
| 6,083,257 A * | 7/2000 | Taylor et al. | 623/1.46 |
| 6,087,479 A | 7/2000 | Stamler et al. | |

(Continued)

FOREIGN PATENT DOCUMENTS

EP    1 103 234 A1    5/2001

(Continued)

OTHER PUBLICATIONS

A pending U.S. Appl. No. 09/374,425, filed Aug. 13, 1999 for which the issue fee has been paid, which is a continuation of U.S. Appl. No. 09/072,944, filed May 5, 1998.

(Continued)

*Primary Examiner*—Suzette Gherbi  
(74) *Attorney, Agent, or Firm*—Jones Day

(57) ABSTRACT

A medical device for delivering a biologically active material into a body tissue, comprising struts and optionally the biologically active material. In an embodiment, the medical device comprises non-structural elements integral with the struts. A method for designing such medical device are also disclosed. Another embodiment is a medical device having an outer surface comprising a middle section and end sections. The end sections have a greater available surface area, greater affinity for or a greater amount of the biologically active material per unit length of the outer surface than the middle section. The middle section may be covered with a barrier layer. Another embodiment is a medical device comprising a rectangular portion having a greater capacity for carrying a biologically active material per unit length of the outer surface. A method for delivering a biologically active material to a body tissue is also disclosed.

15 Claims, 10 Drawing Sheets

U.S. PATENT DOCUMENTS

| | | | |
|---|---|---|---|
| 6,099,562 | A | 8/2000 | Ding et al. |
| 6,106,548 | A | 8/2000 | Roubin et al. |
| 6,192,271 | B1 | 2/2001 | Hayman |
| 6,197,013 | B1 | 3/2001 | Reed et al. |
| 6,273,913 | B1 * | 8/2001 | Wright et al. .............. 623/1.42 |
| 6,287,628 | B1 | 9/2001 | Hossainy et al. |
| 6,379,379 | B1 | 4/2002 | Wang |
| 6,383,215 | B1 | 5/2002 | Sass |
| 6,451,050 | B1 | 9/2002 | Rudakov et al. |
| 6,458,152 | B1 | 10/2002 | Khosravi et al. |
| 6,471,979 | B2 | 10/2002 | New et al. |
| 6,471,980 | B2 | 10/2002 | Sirhan et al. |
| 6,506,437 | B1 * | 1/2003 | Harish et al. .............. 427/2.25 |
| 6,517,889 | B1 | 2/2003 | Jayaraman |
| 6,540,777 | B2 * | 4/2003 | Stenzel ...................... 623/1.16 |
| 6,562,065 | B1 * | 5/2003 | Shanley ..................... 623/1.15 |
| 6,764,505 | B1 | 7/2004 | Hossainy et al. |
| 6,981,985 | B2 * | 1/2006 | Brown et al. .............. 623/1.15 |
| 2002/0068969 | A1 * | 6/2002 | Shanley et al. ............ 623/1.16 |
| 2002/0107563 | A1 * | 8/2002 | Shanley ..................... 623/1.15 |
| 2003/0069630 | A1 * | 4/2003 | Burgermeister et al. ... 623/1.15 |
| 2004/0006382 | A1 * | 1/2004 | Sohier ....................... 623/1.15 |
| 2005/0230039 | A1 * | 10/2005 | Austin et al. ............ 156/272.8 |

FOREIGN PATENT DOCUMENTS

| | | |
|---|---|---|
| WO | WO 98/36784 | 8/1998 |

OTHER PUBLICATIONS

A pending U.S. Appl. No. 10/017,004, filed Dec. 14, 2001, which is a continuation of co-pending U.S. Appl. No. 09/374,425, filed Aug. 13, 1999, which is a continuation of U.S. Appl. No. 09/072,944, filed May 5, 1998.

Hwang et al., *Circulation*, Jul. 31, 2001, pp. 600-605 (http://www.circulationaha.org).

Nikol et al., *Journal of Invasive Cardiology*, 10(8): 506-514, 1998 (http://www.medscape.com/HMP/JIC/1998/v10.n08/jic1008.16.niko-01.html).

Alexander, *SLACK Incorporated Newspaper*, http://slackinc.com/general/cardio/199811/candywrap.asp.

Isner, *American College of Cardiology 48th Annual Scientific Session* Mar. 7-10, 1999.

Creel, *Circulation Research* Apr. 28, 2000 pp. 879-884 (http://www.circresaha.org).

Farb et al., Circulation Jul. 24, 2001 pp. 473-479 (http://www.circulationaha.org).

Rajani, *BHJ*, http://www.bhj.org/journal/1999_4102_apr99/sp_228.htm.

Sigwart, *Lancet*, Jul. 24, 1999, http://www.findarticles.com/cf_0/m0833-9175_354/55404149/p1/article.jhtml.

Peng et al., Biomaterials 1996, vol. 17 No. 7 pp. 685-694.

* cited by examiner

MEDICAL DEVICE FOR DELIVERING BIOLOGICALLY ACTIVE MATERIAL

FIELD OF THE INVENTION

This invention relates generally to medical devices, such as stents, for delivering a biologically active material to a desired location within the body of a patient. More particularly, the invention is directed to a medical device comprising a plurality of struts and a plurality of non-structural elements integral with the struts, wherein the struts and the non-structural elements comprise the biologically active material. The invention is also directed to a method for delivering the biologically active material to body tissue of a patient by inserting this medical device into body of the patient, and further a method for designing such medical device.

The invention is also directed to a medical device comprising a plurality of struts and having an outer surface wherein the outer surface which has a middle section and end sections. The end sections of the outer surface either (1) contain a greater amount of a biologically active material per unit length of the outer surface or (2) have a greater capacity per unit length to contain such material than the middle section of the outer surface by having a greater surface area per unit length of the outer surface than the middle section or having a greater affinity for the biologically active material per unit length of the outer surface than the middle section.

BACKGROUND OF THE INVENTION

A variety of medical conditions have been treated by introducing an insertable medical device having a coating for release of a biologically active material. For example, various types of biologically active material-coated medical devices, such as stents, have been proposed for localized delivery of the biologically active material to a body lumen. See, e.g., U.S. Pat. No. 6,099,562 to Ding et al. However, it has been noted that, with existing coated medical devices, the release profile of a biologically active material may not be uniform along the entire length of the medical device.

For example, even if a biologically active material having a pharmacological effect is delivered to a body tissue, such effect may not result if the concentration of the biologically active material in the body tissue is below a certain concentration. Such concentration is referred to as the minimum effective concentration ($C_{min}$) of the biologically active material in the body tissue. Each biologically active material has different $C_{min}$. $C_{min}$ of a biologically active material also varies depending on the type of body tissue to which it is delivered. On the other hand, a biologically active material becomes toxic if its concentration is higher than a certain concentration. Such concentration is referred to as the maximum effective concentration $C_{max}$. In addition, it is insufficient that the mean concentration of the biologically active material delivered through out the body tissue to be treated is greater than $C_{min}$ and smaller than $C_{max}$. The concentration of the biologically active material at each and every area throughout the body tissue to be treated should be equal to or greater than $C_{min}$ but equal to or smaller than $C_{max}$ of the biologically active material. For instance, when a coated stent comprised of struts, such as the stent shown in FIG. 1, is used as a medical device for delivering a hydrophobic biologically active material, concentrations of the biologically active material may significantly differ between the regions of the tissue adjacent to the struts and the regions of the tissue farther from the struts. See Hwang et al., http://www.circulationaha.org (accepted in April 2001). Even if the mean concentration of the biologically active material in the tissue surrounding the stent is above $C_{min}$ of the biologically active material and at or under $C_{max}$, the concentrations at certain regions of the tissue to be treated, which are farther from the struts, may not reach $C_{min}$. Also, if the amount of the biologically active material in the coating is increased to achieve a concentration higher than $C_{min}$ at all regions of the tissue to be treated, then the concentrations at regions of the tissue adjacent to the struts may exceed the toxic levels, as explained below using the figures.

In FIG. 1, the coated stent 10 is placed in a blood vessel 15 having a vessel wall 12 to be treated. This vessel wall is surrounded by tissue 12a. The biologically active material coated on struts 13 of the stent 10 is released into the vessel wall 12 to be treated. FIG. 2 is a cross sectional view along line A of the stent 10 in FIG. 1. FIG. 2 also shows the concentration levels of the biologically active material in each area surrounding the struts 13 at a certain time after the insertion of the stent into the vessel 15. The area adjacent to the struts, i.e., the area between the struts 13 and line 16, has a concentration level at or below $C_{max}$, which is just below the toxic level. The farther from the struts 13 the tissue to be treated is located, the lower the concentration of biologically active material delivered to the tissue becomes. However, the area between line 18 and line 19 has the concentration level at or higher than $C_{min}$. A concentration of the biologically active material in the area outside line 19 is below $C_{min}$.

Also, FIGS. 2A and 2B clearly show that there are gaps between each strut 13 wherein the vessel wall to be treated does not receive sufficient biologically active material to have $C_{min}$. The areas within line 19, i.e., having concentrations above $C_{min}$, may be increased in size to include more area of the vessel wall to be treated 12, if the amount of the biologically active material on the struts 13 is increased. However, by doing so, the concentration of the biologically active material in the area adjacent to the struts 13 may exceed the toxic level. Accordingly, there is a need for a medical device comprising a plurality of struts that can achieve the biologically active material concentration that is above $C_{min}$ and below toxic levels throughout the tissue.

Also, with existing coated medical devices, generally, the coating is uniformly applied along the entire length of the device or surface of the device. For example, conventional coated stents are coated uniformly along the entire length of the surface of the device. The biologically active material-concentration-profile along the length of the coated surface may be in the shape of a bell-curve, wherein the concentration of the biologically active material released at the middle of the surface is greater than the concentration of the biologically active material released at the ends of the coated surface. This uneven concentration-profile along the length of the coated surface may lead to the application of an inadequate or sub-optimal dosage of the biologically active material to the body tissue located at the ends of the coated surface. It is possible that such uneven local concentration of the biologically active material along the length of the coated surface of the medical device may lead to undesired effects. For example, in the case of a biologically active material-coated stent used to prevent or treat restenosis, if the amount of biologically active material delivered to the tissue located at the ends of the stent is sub-optimal, it is possible that restenosis may occur in such tissue.

The biologically active material dosage at the tissue located at the ends of the coated surface of the medical device can be increased if the concentration or amount of the biologically active material is increased along the entire length of the surface. However, by increasing the concentration or amount of biologically active material released along the entire surface, the dosage delivered to tissue located at the middle of the surface may be too great or even at toxic levels. Thus, there is a need for a medical device that can realize a more uniform concentration-profile for biologically active material along the entire length of a coated surface of a medical device and avoid the possibility of undesired effects accompanied by an uneven biologically active material concentration-profile.

Moreover, medical devices wherein a biologically active material is uniformly coated on the entire outer surface of the medical devices that is exposed to body tissue are generally used to deliver such biologically active material to specific parts of such body tissue. For instance, such devices are used to treat lesions in body lumen. However, because the entire outer surface of the device contains the biologically active material, this biologically active material will be delivered to healthy body tissue in addition to the lesion. Treatment of healthy tissue with the biologically active material is not only unnecessary but maybe harmful. Accordingly, there is a need for a medical device that can realize an asymmetry release-profile of biologically active material to deliver such material to only a limited region of the body tissue that requires the biologically active material.

SUMMARY OF THE INVENTION

These and other objectives are accomplished by the present invention. To achieve the aforementioned objectives, we have invented a medical device for delivering a biologically active material into a body tissue of a patient; a method for designing such device; and a method for delivery of a biologically active material to a body tissue.

The medical device of the invention is a medical device for delivery of biologically active materials to a body tissue of a patient in need of treatment. The medical device comprises struts and non-structural elements integral with the struts, and those struts and non-structural elements comprise the biologically active material. In an embodiment, the medical device comprises a tubular portion having an outer surface, and the non-structural elements are distributed throughout the outer surface. In another embodiment, the non-structural elements are located in a radially asymmetric distribution on the outer surface. In yet another embodiment, the outer surface has end sections and a middle section, and the end sections comprise a greater number of the non-structural elements per unit length of the outer surface than the middle section.

The present invention is also directed to a method for delivering a biologically active material to body tissue of a patient which comprises inserting the above-mentioned medical device into the body of the patient.

Further, the present invention is directed to a method for designing such medical device. The method comprises: providing a preliminary medical device comprising struts in a geometric pattern wherein the struts comprise the biologically active material; determining a concentration-profile for the biologically active material which is released from the preliminary medical device; and modifying the geometric pattern of the struts of the preliminary medical device by incorporating non-structural elements comprising the biologically active material that are integral with the struts to achieve more desired distribution of the biologically active material in the body tissue.

The present invention is also directed to a medical device insertable into the body of a patient. The medical device has an outer surface comprising struts, and the outer surface has a middle section and end sections. The end sections have a greater available surface area per unit length of the outer surface than the middle section. In another embodiment, the end sections have greater affinity for the biologically active material per unit length of the outer surface than the middle section. In yet another embodiment, the end sections have a greater amount of the biologically active material per unit length of the outer surface than the middle section. Further, in another embodiment, at least a part of each of the middle section and the end sections is covered with a coating comprising the biologically active material, and the middle section comprises a barrier layer placed over the coating covering the middle section.

Moreover, the present invention provides another embodiment of the medical device for treating body tissue. The medical device comprises an outer surface comprising struts. The outer surface has a rectangular portion having a greater capacity for carrying or containing a biologically active material per unit length of the outer surface than the parts of the outer surface that are outside the rectangular portion. In the alternative, the rectangular portion may have a greater affinity for the biologically active material. The present invention is also directed to a method for delivering a biologically active material by inserting the above-mentioned medical device comprising the biologically active material in such a way that the rectangular portion is in direct contact with the body tissue in need of treatment.

BRIEF DESCRIPTION OF THE DRAWINGS

FIGS. 2A and 2B also show areas of body tissue having different concentration levels of the biologically active material.

FIGS. 4A and 4B also show areas having different concentration levels of the biologically active material.

DETAILED DESCRIPTION OF THE INVENTION

1. Medical Device for Delivering Biologically Active Material with Desired Distribution

1.1 Non-Structural Elements

Even if a biologically active material having a pharmacological effect is delivered to a body tissue, such effect may not result if the concentration of the biologically active material in the body tissue is below a certain concentration ($C_{min}$). On the other hand, a biologically active material becomes toxic if its concentration is higher than a certain concentration ($C_{max}$). The concentration of the biologically active material at each and every area throughout the body tissue to be treated should be at or above $C_{min}$ but at or under $C_{max}$ of the biologically active material.

When the medical device is comprised of a plurality of struts comprising a biologically active material, the body tissue located at or near a center of each "cell" of the medical device, i.e., openings between the struts, tends to have the lowest concentration of the biologically active material. Such concentration can be below $C_{min}$. This is particularly true when the biologically active material is hydrophobic. When the concentration of the biologically active material in the tissue located at the center of each cell is lower than $C_{min}$, the concentration can be increased by increasing the amount of the biologically active material coated on outer surface of each strut. However, then the concentration at the tissue adjacent to the struts may exceed $C_{max}$.

Figure 1:
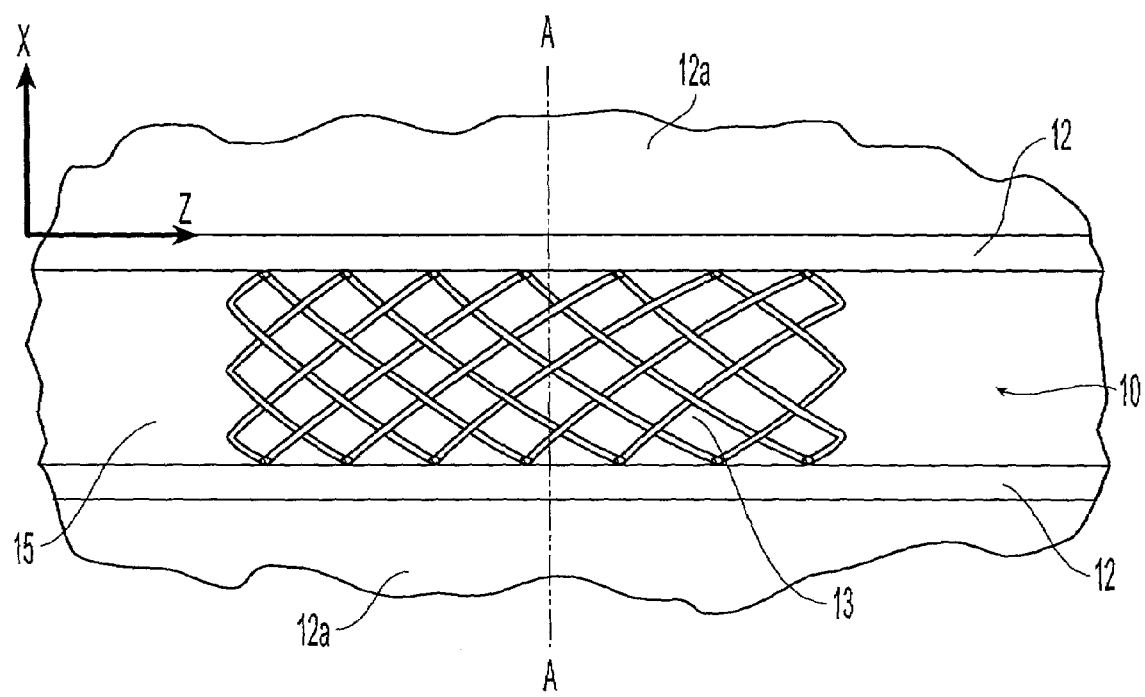
FIG. 1 depicts a side view of a stent without non-structural elements in a cross-sectioned blood vessel. The stent is coated with a biologically active material.
Figure 2A:
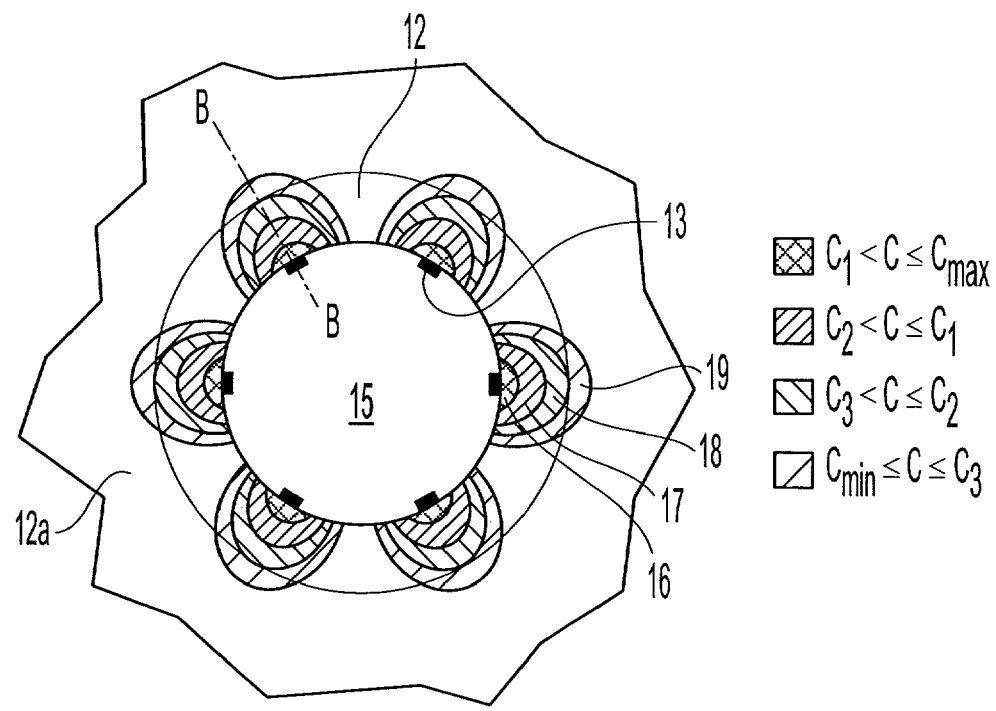
FIGS. 2A and 2B depict cross sectional views of the stent and blood vessel of FIG. 1 along line A-A and line B-B (shown in FIG. 2A), respectively.
Figure 2B:
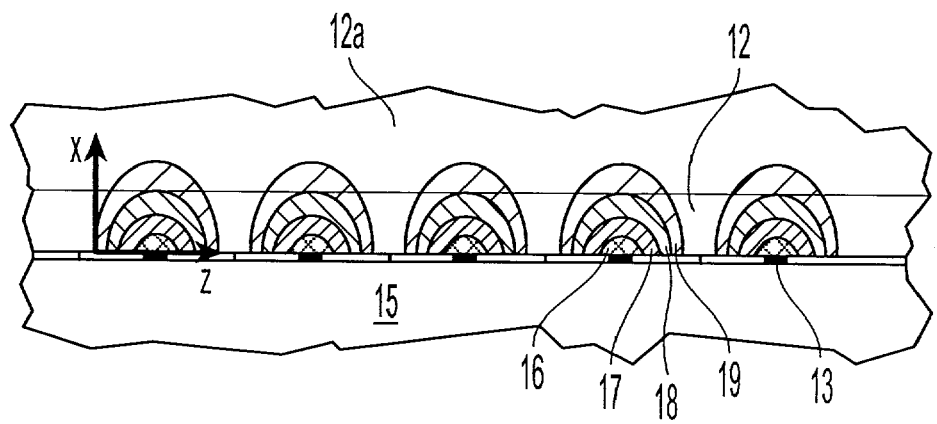

For example, FIG. 1 depicts a coated stent 10 having a conventional geometric pattern, which is placed in a blood vessel 15 having a vessel wall 12 to be treated. The biologically active material coated on struts 13 of the stent 10 is released into the vessel wall 12 to be treated. FIGS. 2A and 2B show cross sectional views along line A-A and line B-B (shown in FIG. 2A) of the stent 10 in FIG. 1 and the concentration levels of the biologically active material in each area surrounding the struts 13 at a certain time after the stent 10 was inserted into the vessel 15. The area adjacent to the struts, i.e., the area between the struts 13 and line 16 has a concentration level at or below $C_{max}$, which is just below the toxic level. The farther from the struts 13 the area is located, the lower the concentration becomes. Thus, the concentration levels gradually decrease from the area between lines 16 and 17, the area between 17 and 18, to between 18 and 19. The area between line 18 and line 19 has a concentration level at or higher than $C_{min}$. A concentration of the biologically active material in the area outside line 19 is below $C_{min}$, and thus the pharmacological effects of the biologically active material does not result in the area.

Furthermore, FIGS. 2A and 2B clearly show that there are gaps between each strut 13, i.e., near the center of cells, wherein the vessel wall to be treated does not receive sufficient biologically active material to have $C_{min}$. The size of the area within line 19, i.e., the areas having the concentrations above $C_{min}$, may be increased to include the entire area of the vessel wall to be treated 12 if the amount of the biologically active material on the struts 13 is increased. However, by doing so, the area adjacent to the struts 13 may be also increased and exceed the toxic level. Therefore, there is a need for a medical device that can ensure the concentration of the biologically active material throughout the body tissue to be treated is at least $C_{min}$ and at most $C_{max}$.

To achieve such a desired distribution of a biologically active material throughout the body tissue to be treated, the embodiments of the medical device of the present invention comprise a plurality of struts and a plurality of non-structural elements integral to the struts. The struts and non-structural elements comprise the biologically active material. These non-structural elements are used to adjust the distribution of the biologically active material in the body tissue so that the desired concentration-profile for the biologically active material released from the medical device into the body tissue can be achieved. For instance, the medical device of the present invention can achieve concentrations higher than $C_{min}$ at the tissue located at the center of cells without increasing the local concentration at an area adjacent to the struts higher than $C_{max}$.

Figure 3:
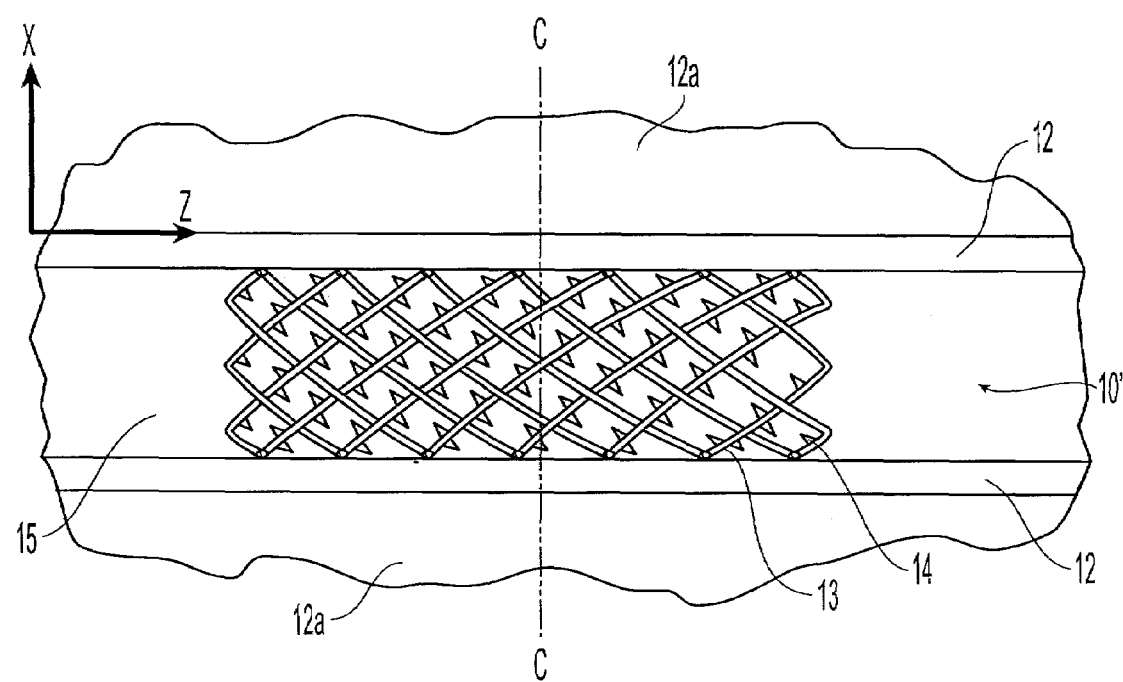
FIG. 3 depicts a side view of a stent with non-structural elements in a cross-sectioned blood vessel. The stent is coated with a biologically active material.
Figure 4A:
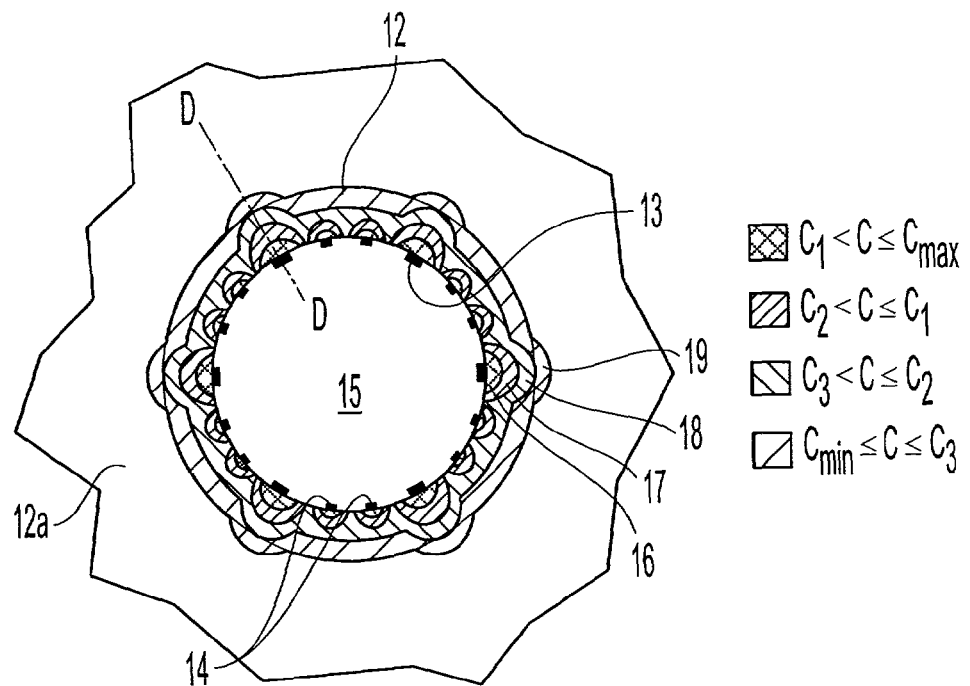
FIG. 4A and 4B depict cross sectional views of the stent and blood vessel of FIG. 3 along line C-C and line D-D (shown in FIG. 4A), respectively.
Figure 4B:
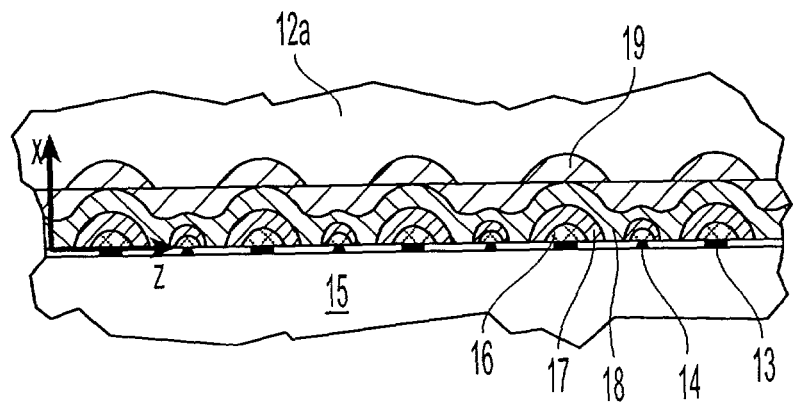

An example is shown in FIGS. 3, 4A and 4B. FIG. 3 depicts a coated stent 10' which is obtained by modifying the conventional geometric pattern of stent 10 shown in FIG. 1 by incorporating non-structural elements 14 integral to the struts 13. The stent 10' is placed in a blood vessel 15 having a vessel wall 12 to be treated. The biologically active material coated on struts 13 and non-structural elements 14 of the stent 10' is released into the vessel wall 12 to be treated and tissue 12a surrounding the vessel wall 12. FIGS. 4A and 4B show cross sectional views along line C-C and D-D (shown in FIG. 4A) of the stent 10' in FIG. 3 and the concentration levels of the biologically active material in each area surrounding the struts 13 and the nonstructural elements 14 at a certain time after the stent 10' was inserted in the vessel 15. The area adjacent to the struts, i.e., the area between the struts 13 or the nonstructural elements 14 and line 16 has a concentration level from at or below $C_{max}$, which is just below the toxic level. The farther from the struts 13 or the nonstructural elements 14 the area is located, the lower the concentration becomes. The area between line 18 and line 19 has the concentration level at or higher than $C_{min}$. FIG. 4 clearly shows that the stent 10' can achieve concentrations higher than $C_{min}$ throughout the entire area of the vessel wall to be treated 12, even at areas located at the center of cells, without increasing the concentration at areas adjacent to the struts above $C_{max}$.

The term "non-structural element" refers to an element integral with a strut, which can project from the strut or can be located along the strut. Such non-structural elements have substantially no effect on the mechanical properties of the struts, such as, for example, (1) radial strength, (2) longitudinal flexibility, (3) expansion ratio, (4) trackability and (5) profile of a medical device comprising the plurality of struts. In embodiments of the medical device of the present invention, the non-structural elements are integral with the struts, namely, they are generally made from the same material as the struts and are formed as a continuous part of the struts. Preferably, the non-structural elements and struts may be manufactured simultaneously; for example, struts having non-structural elements can be laser-ablated from a plate of metal or polymer.

Figure 5:
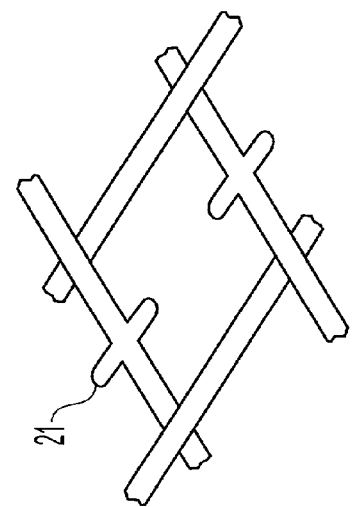
FIG. 5 depicts struts of a conventional expandable stent.
Figure 6:
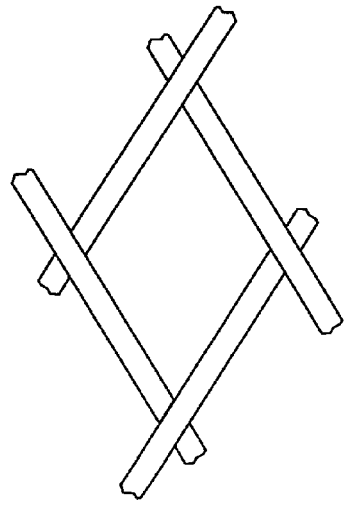
FIGS. 6-14, each depicts struts having non-functional elements integral with the struts.
Figure 7:
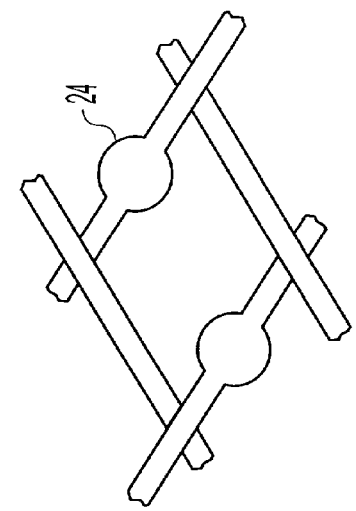
Figure 8:
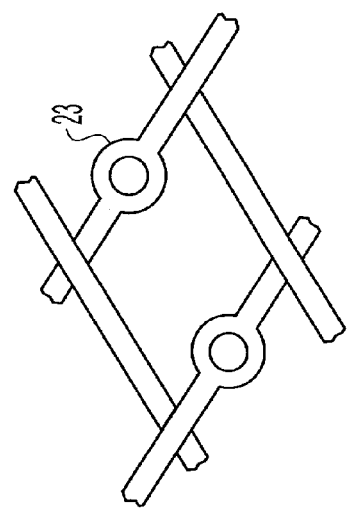
Figure 9:
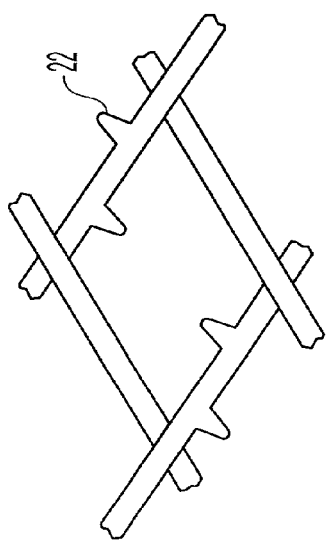
Figure 11:
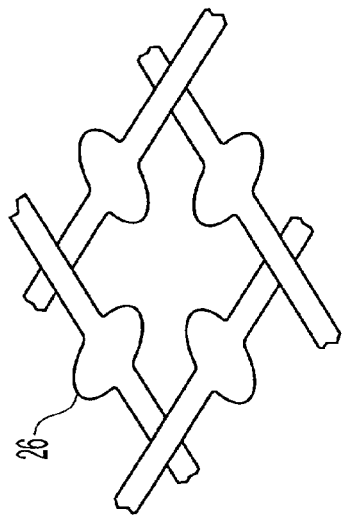
Figure 10:
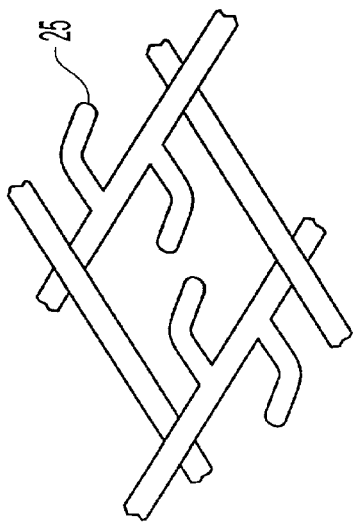
Figure 14:
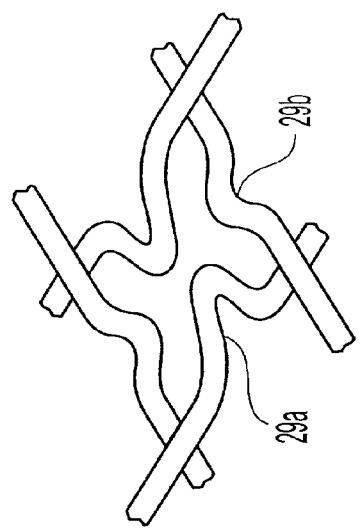
Figure 13:
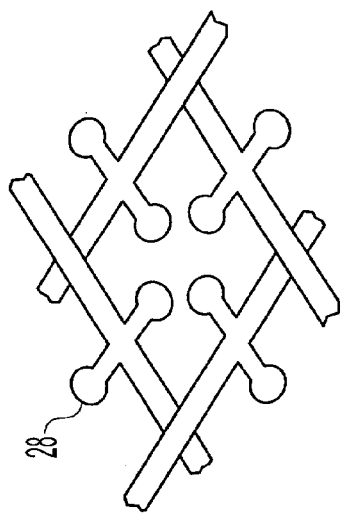
Figure 12:
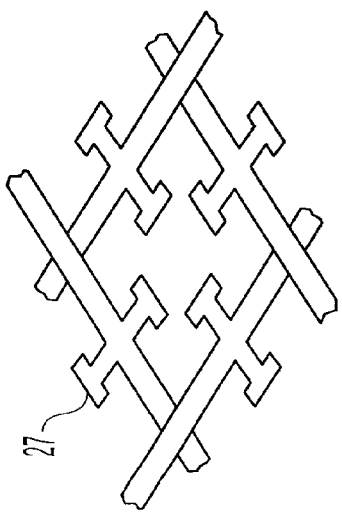

FIG. 5 depicts example of conventional struts without non-structural element, and FIGS. 6-14 depict examples of non-structural elements integral with the conventional struts. Shapes of the non-structural elements include, but not limited to, a straight rod (21 in FIG. 6), a cone (22 in FIG. 7), a truncated cone (not shown), a hoop (23 in FIG. 8), a knot (24 in FIG. 9), a bent rod (25 in FIG. 10), an oval (26 in FIG. 11), and a rod having heads at its ends (27 in FIG. 12 and 28 in FIG. 13). Bends in the struts (29a and 29b in FIG. 14) can be used as non-structural elements so long as they do not affect the mechanical properties of the struts.

This embodiment of the medical device of the present invention can be used for delivering any kind of biologically active material. Preferably, the biologically active material is hydrophobic, e.g., paclitaxel, actinomycin, sirolimus, tacrolimus, everolimus, dexamethasone, halofuginone and hydrophobic nitric oxide adducts. Other examples of the biologically active material, coatings containing the biologically active material, and examples of the medical device are explained later in this application.

1.2 Designing Medical Devices Having Struts and Non-Structural Elements

The present invention is directed to a method for designing a medical device comprising a plurality of struts and non-structural elements integral with the struts for delivering a biologically active material to a body tissue of a patient. As explained above, when the struts are placed in a certain geometric pattern, the concentration of a biologically active material at a center of each cell may not reach $C_{min}$ of the biologically active material. However, the method of the present invention provides a geometric pattern of the struts in which the concentration of a biologically active material above $C_{min}$ can be achieved throughout the body tissue to be treated without increasing the concentration at the tissue located adjacent to the struts above $C_{max}$.

In the method of the invention, a preliminary medical device comprising a plurality of struts in a geometric pattern is modified by incorporating non-structural elements to the struts to improve the concentration-profile for the biologically active material released from the device to the body tissue to be treated. Any medical device comprising a plurality of struts in a geometric pattern, such as stent, can be used as a preliminary medical device for the method of the invention provided that the struts comprises a biologically active material.

In the method of the present invention, a concentration-profile for the biologically active material delivered to the body tissue from the preliminary medical device is determined. From this profile, the areas of tissue in which the concentration of the biologically active material is below $C_{min}$ can be determined. Such areas are then correlated to the parts of the geometric pattern of the struts of the preliminary medical device that were in contact with or near such areas.

The determination of such concentration-profile can be conducted by actually measuring concentrations using the biologically active material in vitro with a tissue model, which is similar to the body tissue to be treated, such as cannulated animal arteries with surrounding tissue or an artificial tissue, or in vivo with an animal model, such as rabbits or pigs. The biologically active material used for the experiment may be labeled with a fluorescence, a radioactive material or dye. Such labeled biologically active material is coated on the medical device, and then the coated medical device is inserted into the tissue model, or artificial tissue, or implanted in an animal. Alternatively, the biologically active material may be detected using standard GLP separation, mass spectroscopy or other direct analytical methods. After insertion, the tissue may be appropriately sectioned, and the concentration-profile for the labeled biologically active material is measured by a means appropriate to the label employed for the experiment. However, a necessary care should be taken that the label would not greatly affect the diffusion of the biologically active material itself.

However, the concentration-profile may also be determined by mathematical simulation. For example, assuming a simple diffusion model, such simulation can be conducted by using the following conditions and equations:

$$\frac{\partial C}{\partial t} = D_x\left(\frac{\partial^2 C}{\partial x^2}\right) + D_z\left(\frac{\partial^2 C}{\partial z^2}\right)$$

wherein C refers to a concentration of the biologically active material in the body tissue, x refers to a distance from the medical device along x axis which is perpendicular to a boundary between the medical device and the body tissue, z refers to a distance from the medical device along z axis which is parallel to the boundary, Dx refers to a diffusion coefficient of the biologically active material in direction along x axis, Dz refers to a diffusion coefficient of the biologically active material in a direction along z axis. For example, such x axis and z axis are shown in FIGS. 1, 2B, 3 and 4B. Dx and Dz can be determined by the experiments using the labeled biologically active material in vitro or in vivo as described above. C=0 at t=0, wherein boundary conditions are as follows:

(i) at a common boundary between the struts and the body tissue (at x=0):

$$D_x \frac{\partial C}{\partial x} = h_1(C - C_\Gamma)$$

wherein $C_\Gamma$ refers to a concentration of the biologically active material in the struts, and $h_1$ refers to a mass transfer coefficient. Value of $h_1$ can be determined by the same experiments described above or determined by assumption based on the information known to one skilled in the art;

(ii) at a boundary between blood flow and the body tissue (at x=0):

$$D_x \frac{\partial C}{\partial x} = h_2(C - 0)$$

wherein $h_2$ refers to another mass transfer coefficient. Value of $h_2$ can be determined by the same experiment mentioned above or determined by assumption based on the information known to one skilled in the art;

(iii) at an adventitial side of vascular wall (at x=L):

$$D_x \frac{\partial C}{\partial x} = -h_3(C - 0)$$

wherein $h_3$ is yet another mass transfer coefficient, and L is a width of a region of interest. Value of $h_3$ can be determined by the same experiment mentioned above or determined by assumption based on the information known to one skilled in the art; and (iv) "symmetry" (no-flux) boundary conditions at certain cross-sections perpendicular to z axis:

$$\frac{\partial C}{\partial z}(z = 0) = \frac{\partial C}{\partial z}(z = L_z) = 0$$

wherein Lz is the length along z axis of a region of interest.

Although a simplified model based on two diffusion coefficients of the biologically active material in two directions, i.e., depth of the tissue penetration and the distance diffused, is described above as an example, there are more complex models can be also employed for the method of the present invention. Such complex models may further account for other variables, such as convection, vessel wall inhomogeneties, the type of cells, the lesions, the variabilities brought by different coatings or coating porosity, blood flow, body temperature, blood pressure, and/or pressure of the implant against the vessel wall.

Subsequent to determining the concentration-profile for the biologically active material which is released from the preliminary medical device, the geometric pattern of the preliminary medical device is modified by incorporating a plurality of non-functional elements that are integral with the struts to achieve more desired distribution of the biologically active material in the body tissue to be treated. The non-structural elements also comprise the biologically active material. For example, the area of tissue in which the concentration of the biologically active material is below $C_{min}$ is determined from the concentration-profile. Then, it is determined which parts of the geometric pattern of the struts of the preliminary medical device were in contact with or near such areas. The non-structural elements can be incorporated near such parts in the geometric pattern, so that the biologically active material released from the non-structural elements would change the concentration in those areas.

For example, a stent 10 having a plurality of struts 13 in a conventional geometric pattern in FIG. 1 can be provided as the preliminary medical device. The struts 13 are coated with a biologically active material. Then, a concentration-profile in a body tissue for the biologically active material which is released from the struts 13 is determined. An example of such profile is shown in FIGS. 2A and 2B with the cross-sectional views of the stent 10 in the blood vessel 15. The determination of such concentration-profile can be conducted by actually measuring concentrations or by mathematical simulation as mentioned above. According to the obtained concentration-profile, the geometric pattern of the struts 13 of the preliminary stent 10 are modified with non-structural elements 14, for example, as shown in FIG. 3. FIGS. 4A and 4B show the concentration-profile views for the biologically active material in the blood wall 12. When the concentration-profile in the vessel wall to be treated 12 shown in FIGS. 2A-B and 4A-B are compared, in FIGS. 4A-B, the concentrations generally throughout the entire area of the vessel wall to be treated 12 are above $C_{min}$ and below $C_{max}$. It is clear that the modified stent 10' achieves a more desirable concentration-profile in the vessel to be treated 12 with the biologically active material than the preliminary stent 10.

Preferably, after a concentration-profile for the biologically active material in the body tissue which is released from the modified preliminary medical device is determined, if there is an area of the body tissue having the local concentration of the biologically active material lower than $C_{min}$, then the device is modified again by adding non-structural elements to the struts. In addition to or instead of merely adding additional non-structural elements, the non-structural elements which have been already added can be removed or relocated according to the determined concentration-profile. Consequently, a medical device having further improved delivery of the biologically active material is obtained. If necessary, the determination step and the modification step explained above can be repeated as many as possible.

1.3 Medical Device with Radially Asymmetric Area Having Non-Structure Elements

The prior sections (section 1.1 and 1.2) explained how non-structural elements can be added to a preliminary medical device to achieve a more desired concentration-profile for the biologically active material released from the device into body tissue. When the entire outer surface of a medical device, which comprises the plurality of struts and non-structural elements, is used to treat body, the non-structural elements should be positioned uniformly throughout the entire outer surface of the medical device.

Figure 17:
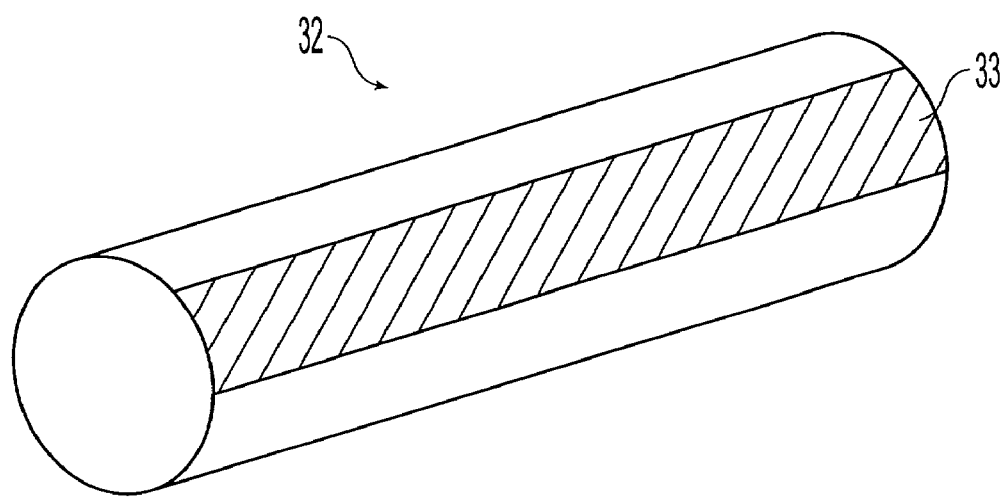
FIG. 17 depicts a simplified view of a stent having a rectangular portion of the outer surface where non-structural elements are located, and the rectangular portion is shown by hatching.
Figure 18:
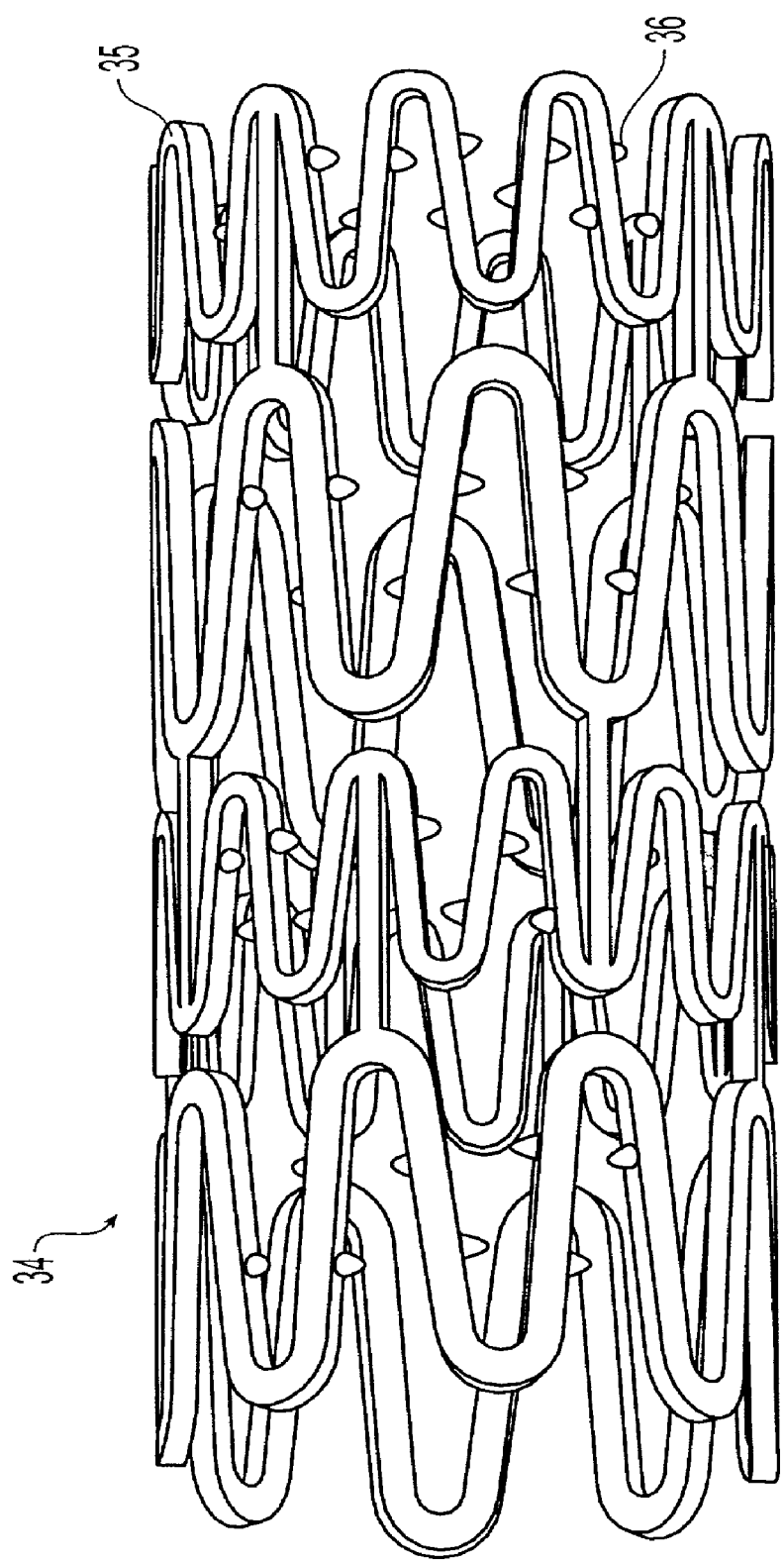
FIG. 18 depicts a perspective view of a stent wherein non-structural elements are located only in a rectangular portion of the outer surface.

However, if the body tissue to be treated is smaller in surface area than the entire outer surface of the medical device, then the non-structural elements do not have to be positioned throughout the entire surface of the medical device. For example, the medical device can comprise a tubular portion comprising an outer surface, such as a stent, which comprises a plurality of struts and a plurality of non-structural elements. The non-structural elements located in a radially asymmetric distribution, such as shown in FIG. 17 where 33 represents the location of the non-structural element on outer surface of a simplified figure of a stent 32. In this figure, the non-structural elements are distributed only in a rectangular portion of the outer surface. FIG. 18 depicts a perspective view of a stent wherein non-structural elements are provided onto the struts only in a rectangular portion of the outer surface. Such rectangular portion may be parallel to longitudinal axis of the tubular portion and may have the same length as that of the tubular portion. The rectangular portion is preferably from about 25% to about 75% of the entire outer surface.

The present invention is also directed to a method for delivering a biologically active material to body tissue using the above-mentioned medical device, which comprises a tubular portion comprising an outer surface which comprises a plurality of struts and a plurality of non-structural elements, and the non-structural elements are located in a radially asymmetric distribution on the outer surface. In the method, the medical device is inserted into body of the patient. Preferably, the non-structural elements are distributed only in a rectangular portion of the outer surface, and the medical device is inserted in such a way that the rectangular portion is in direct contact with the body tissue to be treated. In this way, the body tissue to be treated will receive desired distribution of the biologically active material. On the other hand, the body tissue which does not need to be treated will be exposed to a lesser amount of the biologically active material.

2. Increase Capacity of the End Sections for Carrying or Containing a Biological Active Material In other embodiments of the medical device insertable into the body of a patient of the invention, the medical device comprises an outer surface comprising a plurality of struts, and the end sections of the outer surface have a greater capacity per unit length of the outer surface for carrying or containing a biologically active material than the middle section of the outer surface. Specifically, in one embodiment of the medical device, each strut at the end sections has greater available surface area per unit length of the outer surface than the middle section. In another embodiment, the end sections have a greater affinity for the biologically active material per unit length of the outer surface than the middle section.

The medical device of the present invention may be manufactured with or without a biologically active material by a manufacturer. When the medical device of the present invention is manufactured without a biologically active material, a practitioner (e.g., a medical doctor or a nurse) can apply the biologically active material to the medical device. In either case, since the end sections of the outer surface have a greater capacity per unit length of the outer surface for carrying or containing the biologically active material than the middle section, the end sections will carry a greater amount of the biologically active material when the biologically active material is applied to the medical device without needing to change application method of the biologically active material to the end sections and the method to the middle section. Therefore, when a practitioner applies to the outer surface of the medical device, such as by dipping, a coating composition containing a biologically active material, a larger amount of the biologically active material per unit length of the outer surface will be deposited at the end sections than the middle section.

The term "unit length of the outer surface" refers to the length on an imaginary straight line along the outer surface drawn between a point on an edge of the outer surface and another point on the opposing edge of the outer surface. Therefore, the terms, such as "capacity per unit length of the outer surface," "available surface area per unit length of the outer surface," and "amount per unit length of the outer surface," refer respectively to the capacity, available surface area and amount per unit length of the imaginary straight line explained above.

2.1 Increase Available Surface Area at the End Sections

As explained above, one of the embodiments of the medical device has end sections which have greater available surface area per unit length of the outer surface than that of the middle section. The term "available surface area" refers to a surface area which is available to be coated by a coating composition comprising a biologically active material.

One way of increasing the available surface area of the end sections is to fabricate the outer surface of the medical device using more material at its ends. For example, when the medical device is comprised of struts, the available surface area per unit length of the outer surface in the end sections is increased by adding non-structural elements to the struts. The non-structural elements are explained above (see section 1.1). The end sections comprise a greater number of the non-structural elements per unit length of the outer surface than the middle section. The middle section may have smaller number of the non-structural elements or no non-structural elements.

Figure 15:
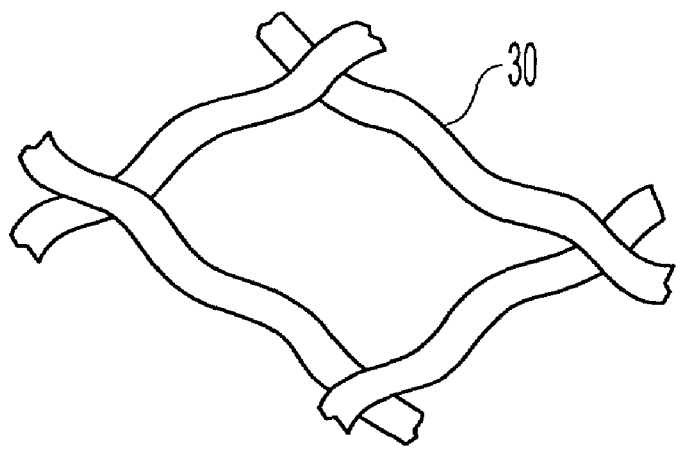
FIG. 15 depicts wavy struts that have greater surface area per unit length of the strut than conventional struts.
Figure 16:
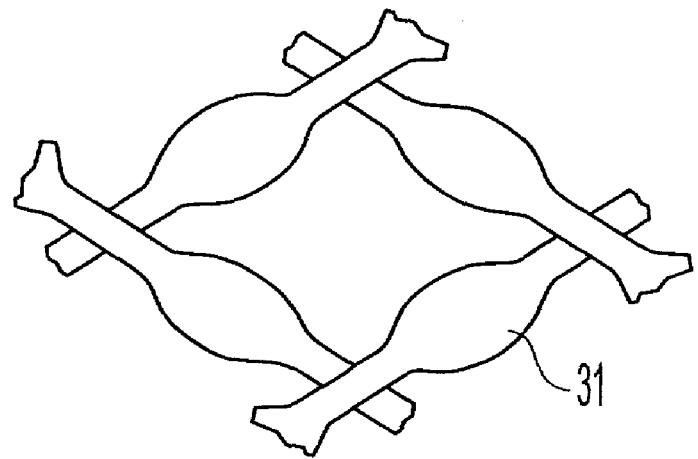
FIG. 16 depicts struts having a greater average diameter per length of the strut than the conventional struts.

Further, the available surface area can be increased by increasing the surface area of the struts themselves. For example, wavy struts 30 shown in FIG. 15 can have more outer surface area per length than straight struts show in FIG. 5. Also, struts having greater average diameter, such as struts which are thicker or wider at certain portion 31 shown in FIG. 16, have greater outer surface area per length than struts which have smaller average diameter. Moreover, the end sections of the outer surface can be made to have greater available surface area by roughing the struts' outer surface or providing indentations or grooves on the struts' surface. The above-mentioned wavy struts, wider or thicker struts, indentations and grooves may have various shapes, so long as such structure does not affect stent's structural functions. For example, the above-mentioned structure should not hinder self-expansion of a self-expanding stent and should not cause any harm to the patient body. The above-mentioned wavy struts, indentations and grooves can be manufactured by laser ablation.

In another embodiment in which the capacity of the end sections to carry or contain the biologically active material is greater than the capacity of the middle section, the end sections of the outer surface are more porous, and the middle section of the surface is relatively less porous. The middle section may also be non-porous. For example, in FIG. 19, the circles 45 and 47 show enlarged portions of the outer surface of the struts 42 of a stent 40 in the middle section 44 and end section 46, respectively. The surface of the struts in the end section 46 has more pores 48 than the surface of the struts at the middle section 44. In such embodiment, the end sections 46 have a greater available surface area per unit length of the outer surface than that of the middle section 44 since the pores 48 increase available surface area.

The end sections of the outer surface may be made porous by forming the end sections of the outer surface themselves from a porous material or by forming the end sections with a non-porous material and then covering the end sections with a porous coating layer. For example, porous metal struts can be prepared by sintering metal, ie., molding or pressing metal particles into a desired shape and heating them to a temperature slightly below the melting point of the metal. Porosity can be changed by using different particle sizes and/or dimensions and/or different temperatures. Also, porous metal struts can be prepared by using metal filaments or fibers. See e.g. U.S. Pat. No. 5,843,172 issued to Yan which discloses examples of struts made of porous materials, which is incorporated herewith by reference.

The end sections of the outer surface may be made porous by coated with a porous coating layer. A porous coating layer may be prepared, for example, by applying a mixture of a polymer, an elutable particulate material and a solvent on a surface to form a layer, and then eluting the elutable particulate material from the layer. The following is a detailed description of suitable materials and methods useful in producing a porous coating layer of the invention.

Polymer(s) useful for forming the porous coating layer should be ones that are biostable, biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers. Since the polymer is being applied to a part of the medical device which undergoes mechanical challenges, e.g. expansion and contraction, the polymers are preferably selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. The polymer is selected to allow the coating to better adhere to the surface of the expandable portion of the medical device when it is subjected to forces or stress. Furthermore, although the porous coating layer can be formed by using a single type of polymer, various combinations of polymers can be employed.

The elutable particulate materials which can be incorporated into the polymer include, but not limited to, polyethylene oxide, polyethylene glycol, polyethylene oxide/polypropylene oxide copolymers, polyhydroxyethyl methacrylate, polyvinylpyrrolidone, polyacrylamide and its copolymers, salts, e.g., sodium chloride, sugars, and elutable biologically active materials such as heparin. The amount of elutable particulate material that is incorporated into the polymer should range from about 20% to 90% by weight of the porous coating layer. Furthermore, to increase the porosity of the coating layer applied to the end sections of the surface, a larger amount of the elutable particulate material can be used to form the porous coating layer at the end sections than are used to form the porous coating layer at the middle section. For example, the amount of the elutable particulate material may be from about 0% to about 40% for the porous coating layer covering the middle section, and about 50% to 90% for the porous coating layer covering at the end sections. Also, a more porous coating layer can be realized by using larger average particle size of the elutable material. For example, the particles may have an average particle size from 60-100 microns for porous coating layer covering the end sections and from 0 to about 30 microns for the porous coating layer covering middle section.

The solvent that is used to form the mixture or slurry of polymer and elutable particulate materials include ones which can dissolve the polymer into solution and do not alter or adversely impact the therapeutic properties of the biologically active material employed. Examples of useful solvents for silicone include tetrahydrofuran (THF), chloroform and dichloromethane. The composition of polymer and elutable particulate material can be applied to the portion of the medical device in a variety of ways. For example, the composition can be spray-coated onto the device or the device can be dipped into the composition. One of skill in the art would be aware of methods for applying the coating to the device.

The thickness of the porous coating layer can range from about 25 µm to 0.5 mm. Preferably, the thickness is about 30 µm to 100 µm. After the composition is applied to the device, it should be cured to produce a polymer containing the particulate material and to evaporate the solvent.

To elute the particulate material from the polymer, a solvent is used. The device can be soaked in the solvent to elute the particulate materials. Other methods of eluting the particulate are apparent to those skilled in the art. The choice of the solvent depends upon the solubility of the elutable particulate material in that solvent. For instance, for water-soluble particulate materials such as heparin, water can be used. For elutable particulate materials that can be dissolved in organic solvents, such organic solvents can be used. Examples of suitable solvents, without limitation, include ethanol, dimethyl sulfoxide, etc.

Another example of a method for preparing a porous coating is a catalyst-free vapor deposition of a coating composition comprising a polyamide, parylene or a parylene derivative. See U.S. Pat. No. 6,299,604 to Ragheb et al., which is incorporated herein by reference.

In another embodiment of the present invention, the surface including the end sections and middle section are covered with a same porous coating layer composition; but the porous coating layer is thicker at the end sections than at the middle section. For example, a porous coating layer is applied to the entire surface, and then another porous coating layer is applied to the end sections while the middle section is covered by a sheath. The thickness of the porous coating layer at the end sections may be from about 80 µm to about 0.5 mm, and that at the middle section may be from about 10 µm to 40 µm. Since there is more porous coating at the end sections, the end sections of the outer surface should have a greater capacity to carry or contain a biologically active material.

2.2 The End Sections with Greater Affinity for the Biological Active Material

In another embodiment of the medical device of the present invention, the end sections of the outer surface have a greater affinity for the biologically active material than the middle section. In particular, the end sections comprise a first matrix material and the middle section comprises a second matrix material. The first matrix material has a greater affinity for the biologically active material of interest than the second matrix material so that the end sections can carry or contain a larger amount of the biologically active material per unit length of the outer surface than the middle section. The end sections and the middle section of the outer surface may be formed from the first matrix material and the second matrix material, respectively. Preferably, the end sections of the outer surface and the middle section of the outer surface are formed of another material and then are covered with a coating comprising each of the matrix materials.

Generally, when a biologically active material used is a hydrophilic, e.g., heparin, then a matrix material comprising a more hydrophilic material has a greater affinity for the biologically active material than another matrix material that is less hydrophilic. When a biologically active material used is a hydrophobic, e.g., paclitaxel, actinomycin, sirolimus (RAPAMYCIN), tacrolimus, everolimus, and dexamethasone, then a matrix material that is more hydrophobic has a greater affinity for the biologically active material than another matrix material that is less hydrophobic.

Examples of suitable hydrophobic polymers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly (vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1- dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly (ethyl methacrylate), poly(2-ethylhexyl methacrylate), poly (n-hexyl methacrylate), poly(phenyl methacrylate), poly(n-propyl methacrylate), poly(octadecyl methacrylate), poly(1, 1-dihydropentadecafluorooctyl methacrylate), poly (heptafluoroisopropyl methacrylate), poly (heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymeric materials characterized by repeating siloxane groups, represented by $R_a SiO_{4-a/2}$, where R is a monovalent substituted or unsubstituted hydrocarbon radical and the value of a is 1 or 2; and naturally occurring hydrophobic polymers such as rubber.

Examples of suitable hydrophilic monomer include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl (meth) acrylate. Polyvinyl alcohol is also an example of hydrophilic polymer. Polyvinyl alcohol may contain a plurality of hydrophilic groups such as hydroxyl, amido, carboxyl, amino, ammonium or sulfonyl (—$SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

The first matrix material and the second matrix material may be prepared using either a hydrophilic polymer or a hydrophobic polymer, or a blend of a hydrophobic polymer and a hydrophilic polymer in a chosen ratio. For example, when the biologically active material is hydrophilic, then the first matrix material may be prepared by blending from about 55% to about 100% hydrophilic polymer and from about 45% to about 0% hydrophobic polymer; and the second matrix material may be prepared by blending from about 55% to about 100% hydrophobic polymer and from about 45% to about 0% hydrophilic polymer. The first matrix material contains a greater amount of the hydrophillic polymer than the second matrix material. When the biologically active material is hydrophobic, then the first matrix material may be prepared by blending from about 55% to about 95% hydrophobic polymer and from about 45% to about 5% hydrophilic polymer; and the second matrix material may be prepared by blending from about 55% to about 95% hydrophilic polymer and from about 45% to about 5% hydrophobic polymer. The first matrix material contains a greater amount of the hydrophobic polymer than the second matrix material.

Again, the outer surface of the medical device of the present invention is, covered with each matrix material, i.e., the end sections with a first matrix material and the middle section with a second matrix material. A first matrix material composition may be prepared and applied by any method to a surface of a medical device to form a coating, such as spraying, dipping, rolling, and electrostatic deposition. Likewise, a second matrix material composition may be prepared and applied by such methods. The first matrix material composition may be applied to the end sections of the outer surface while the middle section is covered to prevent coating the middle section with the first matrix material. Then the second matrix material composition may be applied to the middle section while the end sections are covered. In another embodiment, the second material composition may be applied to the entire outer surface including the middle section and the end sections, then the first matrix material composition may be applied to the end sections while the middle section is covered.

After the matrix material compositions are applied to the outer surface, the surface should be cured to produce matrix material coatings. The thickness of the matrix material coating can range from about 25 μm to about 0.5 mm. Preferably, the thickness is about 30 μm to 100 μm.

2.3 The End Sections with Greater Amount of Chemical Linking Material to Carry or Contain the Biological Active Material In yet another embodiment of the present invention, the capacity of the end sections of the outer surface for carrying or containing a biologically active material can be increased relative to that of the middle section by using an increased amount of chemical linking material to link the biologically active material to the end sections of the outer surface. Specifically, the middle section and end sections of the outer surface are covered with a chemical linking material, and the end sections carry or contain a larger amount of the linking material per unit length of outer surface than the middle section. The chemical linking material allows the biologically active material to attach to the outer surface. "Linking materials" may be any material which can be coupled to a biologically active material by any bond that are known in the relevant art including but not limited to, Van der Waals force, ionic bond, covalent bond, hydrogen bond or chemical cross-linking.

For example, U.S. Pat. No. 5,356,433 to Rowland et al., discloses that polysaccharides can be immobilized onto metallic surfaces by applying an organosilane coating with amine functionality and then applying a polysaccharide using carbodiimide as a coupling agent. In the present invention, if the organosilane with amine functionality is used as a linking material, the amount of this material per unit length of the outer surface at the end sections is greater than that at the middle section. In that way, larger amount of a polysaccharide, which is a biologically active material, can coupled to the end sections.

Also, U.S. Pat. No. 5,336,518 to Narayanan et al. discloses that a polysaccharide can be immobilized on a surface by applying a coat of heptafluorobutylmethacrylate (HFBMA) by radiofrequency (RF) plasma deposition, creating functional groups on the surface by RF plasma with water vapor, and then applying the polysaccharide using carbodiimide. In the present invention, larger amount of HFBMA, a linking material, is applied to the end sections so that larger amount of a polysaccharide, a biologically active material can be coupled to.

3. Radially Asymmetric Medical Devices Having Increased Capacity for Carrying or Containing a Biologically Active Material 3.1 Medical Devices Having Non-Structural Elements Located in a Radially Asymmetric Distribution As explained above, one way to increase the capacity for carrying or containing a biologically active material of the medical device is to increase available surface area. In one embodiment of the medical device of the invention, the available surface area is increased in radially asymmetric manner along the entire outer surface, instead of only at the end sections. One such embodiment where the surface area is increased in a radially asymmetric manner by adding non-structural elements to the outer surface (as to non-structural elements, see section 1.3). For example, only a rectangular portion of the outer surface has the non-structural elements. Such rectangular portion may be parallel to longitudinal axis of the tubular portion and may have the same length as that of the tubular portion. The rectangular portion is preferably from about 25% to about 75% of the entire outer surface. Please see section 1.3 as to a method for delivering a biologically active material to body tissue using such medical device.

3.2 Medical Device Having Radially Asymmetric Increased Available Surface Area or Affinity Another embodiment of the medical device of the invention comprises a tubular portion comprising struts and having an outer surface. A portion of the outer surface has increased available surface or affinity for the biologically active material in such a way that the available surface area or affinity for the biologically active material is radially asymmetric. Please see prior section (section 3.1) as to examples of radially asymmetric distributions. Increased available surface area or increased affinity to the biologically active material can be achieved as explained in the prior sections (sections 2.1 and 2.2). Please see section 1.3 as to a method for delivering a biologically active material to body tissue using such medical device.

4. Suitable Medical Devices

The medical devices of the present invention are insertable into the body of a patient. Namely, at least a portion of such medical devices may be temporary inserted into or semi-permanently or permanently implanted in the body of a patient. Preferably, the medical devices of the present invention comprise a tubular portion which is insertable into the body of a patient. The tubular portion of the medical device need not to be completely cylindrical. For instance, the cross-section of the tubular portion can be any shape, such as rectangle, a triangle, etc., not just a circle.

The medical devices suitable for the present invention include, but are not limited to, stents, surgical staples, catheters, such as central venous catheters and arterial catheters, guidewires, balloons, filters (e.g., vena cava filters), cannulas, cardiac pacemaker leads or lead tips, cardiac defibrillator leads or lead tips, implantable vascular access ports, stent grafts, vascular grafts or other grafts, interluminal paving system, intra-aortic balloon pumps, heart valves, cardiovascular sutures, total artificial hearts and ventricular assist pumps.

Medical devices which are particularly suitable for the present invention include any kind of stent for medical purposes, which are known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco, U.S. Pat. No. 4,886,062 issued to Wiktor and U.S. Pat. No. 5,449,373 issued to Pinchasik et al. A bifurcated stent is also included among the medical devices suitable for the present invention.

The medical devices suitable for the present invention may be fabricated from polymeric and/or metallic materials. Examples of such polymeric materials include polyurethane and its copolymers, silicone and its copolymers, ethylene vinyl-acetate, poly(ethylene terephthalate), thermoplastic elastomer, polyvinyl chloride, polyolephines, cellulosics, polyamides, polyesters, polysulfones, polytetrafluoroethylenes, acrylonitrile butadiene styrene copolymers, acrylics, polyactic acid, polyclycolic acid, polycaprolactone, polyacetal, poly(lactic acid), polylactic acid-polyethylene oxide copolymers, polycarbonate cellulose, collagen and chitins. Examples of suitable metallic materials include metals and alloys based on titanium (e.g., nitinol, nickel titanium alloys, thermo-memory alloy materials), stainless steel, platinum, tantalum, nickel-chrome, certain cobalt alloys including cobalt-chromium-nickel alloys (e.g., Elgiloy® and Phynox®) and gold/platinum alloy. Metallic materials also include clad composite filaments, such as those disclosed in WO 94/16646.

Figure 19:
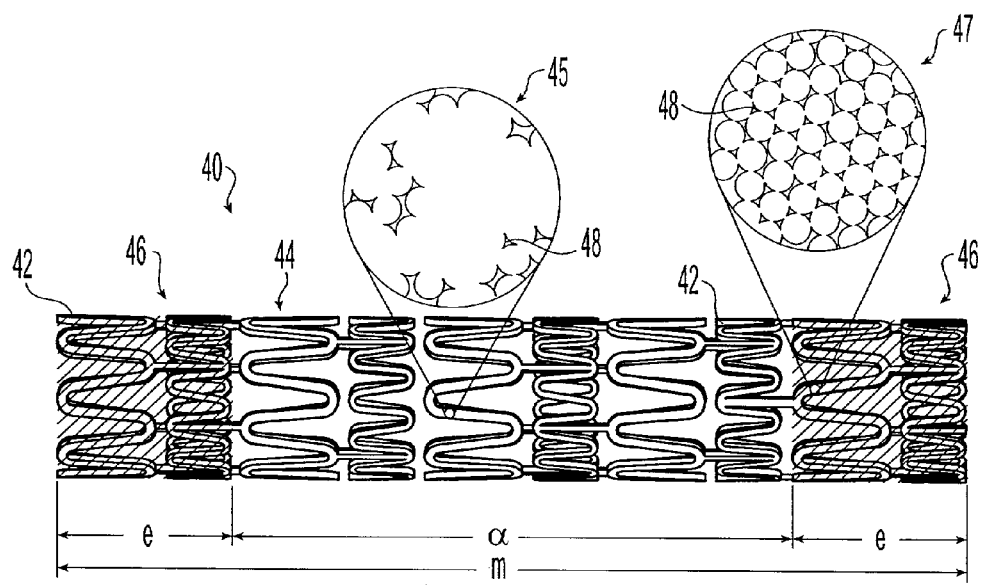
FIG. 19 depicts a stent having end sections and a middle section and comprised of struts, wherein the end sections are comprised of a porous material and the middle section is comprised of a less porous material.
Figure 20:
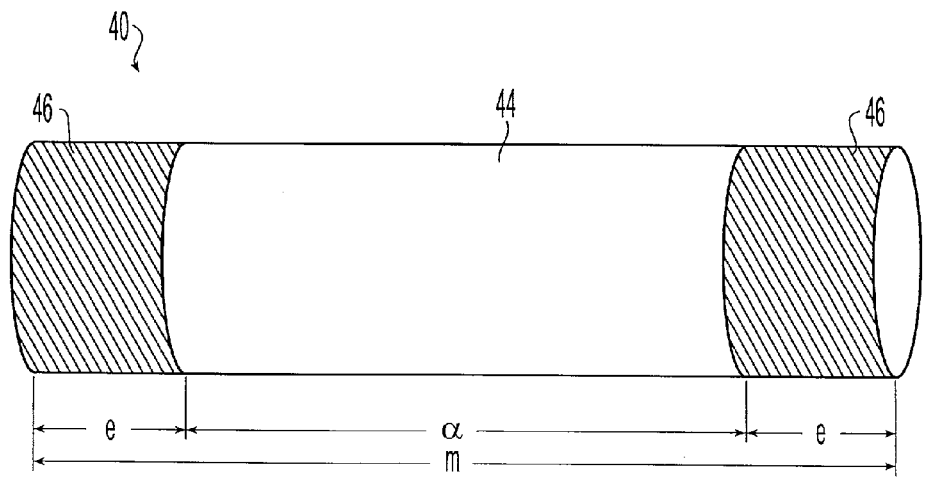
FIG. 20 is a simplified view of a stent which shows the outer surface, having end sections and a middle section.

The medical devices suitable for the present invention also have an outer surface, and the outer surface has end sections and middle section. The term "outer surface" refers to a surface of the medical devices which are to be exposed to body tissue. For example, the tubular structure shown in FIG. 20 is a simplified view of a stent 40. The outer surface of the stent is the surface that is in direct contact with the body tissue when the device is inserted into the body. In the case that the medical device is a stent 40 comprised of struts 42 as shown in FIG. 19, the "outer surface" of the stent refers to the surfaces of the struts which are to directly contact with the body lumen or tissue.

The term "end section" of the outer surface refers to that part of the surface which extends from an end or edge of the tubular portion up to about 25%, preferably from about 3% to about 20% of the entire length of the outer surface. For example, when the medical device is a stent 40 as shown in FIG. 19 or 20, the end section 46 of the outer surface is a ring-shape portion extending from the edge of the outer surface of stent having length e, which is up to 25% of the entire length α of the outer surface of stent. In FIGS. 19 and 20, the end sections are shown as the shaded portions 46.

The term "middle section" refers to the remainder of the outer surface that is surrounded by the end sections as defined above. For example, in FIG. 19 or 20, the middle section 44 is a ring-shape portion having length m, which is surrounded by the end sections.

5. Applying Biologically Active Material to the Outer Surface

As discussed earlier, the biologically active material can be applied to the embodiments described in sections 2.1 to 2.3 when the device is manufactured or later on by a medical professional shortly before the device is inserted into a patient. The biologically active material may be applied to the outer surface of the device obtained as in sections 1.1-1.3, 2.1-2.3 and 3.1-3.2, alone or in conjunction with other materials, such as a polymeric material. For example, in the embodiment where the end sections have a greater available surface area per unit length of the outer surface than the middle section, the biologically active material can be applied to the outer surface in a coating composition containing the biologically active material and a polymeric material. Specifically, a coating composition of biologically active material and polymeric material can be prepared and then applied to the outer surface. However, the biologically active material alone can also be applied to the outer surface of this embodiment.

In the embodiments where a portion of the outer surface has a greater affinity for the biologically active material or where a portion of the outer surface contains more chemical liking material, the biologically active material is preferably applied alone to the outer surface. For instance, in the embodiment having a matrix material with greater affinity for the biologically active material in a portion of the outer surface, the biologically active material can be applied to the matrix material coatings on the outer surface. However, the biologically active material can also be applied to the material along with a polymeric material. Also, the biologically active material can be incorporated into the matrix material coating compositions to form matrix material coatings that already containing biologically active material.

5.1 Coating Compositions and Coating Layers

The coating compositions suitable for the present invention can be applied by any method to a surface of a medical device to form a coating. Examples of such methods are spraying, dipping, rolling, electrostatic deposition and all modern chemical ways of immobilization of bio-molecules to surfaces.

The coating composition used in the present invention may be a solution of a biologically active material in an aqueous or organic solvent. Such coating composition may be applied to a surface, and the solvent may be evaporated. A biologically active material solution may be used when the tubular portion of the medical device has end sections having increased surface area or increased affinity as explained above, especially when the end sections are porous.

Furthermore, coating compositions useful for the present invention may include a polymeric material and optionally a biologically active material dispersed or dissolved in a solvent suitable for the medical device which is known to the skilled artisan. The solvents used to prepare coating compositions include ones which can dissolve the polymeric material into solution and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

A coating of a medical device of the present invention may consist of various kinds of combination of multiple coating layers. For example, the first layer and the second layer may contain different biologically active materials. Alternatively, the first layer and the second layer may contain an identical biologically active material having different concentrations. In one embodiment, either of the first layer or the second layer may be free of biologically active material. For example, when the biologically active solution is applied onto a surface and dried (the first layer), a coating composition free of a biologically active material (the second layer) can be applied over the dried biologically active material.

The polymeric material should be a material that is biocompatible and avoids irritation to body tissue. Examples of the polymeric materials used in the coating composition of the present invention include, but not limited to, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate, styrene-isobutylene copolymers and blends and copolymers thereof. Also, other examples of such polymers include polyurethane (BAYHDROL®, etc.) fibrin, collagen and derivatives thereof, polysaccharides such as celluloses, starches, dextrans, alginates and derivatives, hyaluronic acid, and squalene. Further examples of the polymeric materials used in the coating composition of the present invention include other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

Preferred is polyacrylic acid, available as HYDROPLUS® (Boston Scientific Corporation, Natick, Mass.), and described in U.S. Pat. No. 5,091,205, the disclosure of which is hereby incorporated herein by reference. In a most preferred embodiment of the invention, the polymer is a copolymer of polylactic acid and polycaprolactone.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition adheres better to the surface of the medical device when the device is subjected to forces, stress or mechanical challenge.

A controlled-release coating of a biologically active material may be prepared by a coating composition comprising an appropriate hydrophobic polymer. For example, a controlled-release coating may comprise a coating layer containing a biologically active material and a top coating layer comprising a hydrophobic polymer. Also, a controlled-release coating may be prepared from a coating composition containing a mixture of a hydrophobic polymer and a biologically active material.

The amount of the polymeric material present in the coatings can vary based on the application for the medical device. One skilled in the art is aware of how to determine the desired amount and type of polymeric material used in the coating. The thickness of the coating is not limited, but generally ranges from about 25 μm to about 0.5 mm. Preferably, the thickness is about 30 μm to 100 μm.

5.2 Suitable Biologically Active Material

The term "biologically active material" encompasses therapeutic agents, such as drugs, and also genetic materials and biological materials. The genetic materials mean DNA or RNA, including, without limitation, of DNA/RNA encoding a useful protein stated below, anti-sense DNA/RNA, intended to be inserted into a human body including viral vectors and non-viral vectors. Examples of DNA suitable for the present invention include DNA encoding anti-sense RNA tRNA or rRNA to replace defective or deficient endogenous molecules angiogenic factors including growth factors, such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor cell ccle inhibitors including CD inhibitors thymidine kinase ("TK") and other agents useful for interfering with cell proliferation, and the family of bone morphogenic proteins ("BMP's") as explained below. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g, pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. Alternatively or in addition, molecules capable of inducing an upstream or downstream effect of a BMP can be provided. Such molecules include any of the "hedgehog" proteins, or the DNA's encoding them. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate, azathioprine, halofuginone, adriamycin, actinomycin and mutamycin; endostatin, angiostatin and thymidine kinase inhibitors, and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobramycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalapril.

Also, the biologically active materials of the present invention include nitric oxide adducts, which prevent and/or treat adverse effects associated with use of a medical device in a patient, such as restenosis and damaged blood vessel surface. Typical nitric oxide adducts include nitroglycerin, sodium nitroprusside, S-nitroso-proteins, S-nitroso-thiols, long carbon-chain lipophilic S-nitrosothiols, S-nitrosodithiols, iron-nitrosyl compounds, thionitrates, thionitrites, sydnonimines, furoxans, organic nitrates, and nitrosated amino acids, preferably mono-or poly-nitrosylated proteins, particularly polynitrosated albumin or polymers or aggregates thereof. The albumin is preferably human or bovine, including humanized bovine serum albumin. Such nitric oxide adducts are disclosed in U.S. Pat. No. 6,087,479 to Stamler et al. which is incorporated herein by reference.

A biologically active material may be encapsulated in micro-capsules by the known methods.

5.3 Medical Devices with End Sections that Carry or Contain a Greater Amount of Biologically Active Material than the Middle Section In another embodiment of the invention, a more uniform release-profile for a biologically active material along the length of the outer surface of the medical device may be achieved by preparing a medical device having end sections that carry or contain a greater amount of a biologically active material than the middle section.

In section 2, supra, the medical devices of the present invention having end sections that have increased capacity for carrying or containing a biologically active material were explained. When a coating composition comprising the biologically active material is applied to such medical devices by a conventional method, such as spraying, dipping, rolling, and electrostatic deposition, the end sections will carry or contain a greater amount of the biologically active material per unit length of the outer surface than the middle section of the outer surface.

However, greater amounts of biologically active material at the end sections can also be achieved by controlling the amount of the biologically active material that is applied to the middle and end sections. For instance, additional coating composition containing a biologically active material can be applied to the end sections so that such sections have a thicker coating and hence contain more biologically active material. A method for preparing such medical device comprises, for example, applying a first coating composition containing a biologically active material to the end sections and a middle section of an outer surface, placing a cover over the middle section, applying more of the first coating composition or second coating composition to the end sections of the outer surface. The second coating composition may contain the same biologically active material as the first coating composition having the same or different concentration or may contain a different biologically active material.

Another example of a method useful in allowing more biologically active material to the end sections relative to the middle section involves covering the middle section. In particular, a coating composition containing the desired biologically active material is applied to the middle section and end sections. The middle section is then covered by a sheath or mesh. Such covering can be achieved also by masking using photolithography techniques. Additional coating composition is then applied to the end sections. The covering prevents such additional coating composition from being applied to the middle section so that the end sections will contain relatively more biologically active material.

In yet another embodiment of the medical device of the present invention, a greater amount of biologically active material can be applied to the end sections by applying coating compositions having different concentration of first biologically active material to the middle and end sections. For example, applying a coating composition containing a first concentration of a biologically active material is applied to the end sections while the middle section is covered. Thereafter, a second coating composition having a second concentration of biologically active material, which is smaller than the first concentration, to the middle section. The sections may be covered using sheaths or masking as explained above.

5.4 Medical Device Comprising a Biologically Active Material in a Radially Asymmetric Distribution Yet another embodiment of the medical device of the invention achieves a greater amount of release of a biologically active material to a necessary body tissue. Such medical device comprises an outer surface comprising the biologically active material in a radially asymmetric distribution. For example, a rectangular portion of the outer surface has a greater amount of the biologically active material than the rest of the outer surface. When the medical device comprises a tubular portion, the rectangular portion may be parallel to longitudinal axis of the tubular portion. The rectangular portion may be the same length as that of the tubular portion. A greater amount of the biologically active material can be distributed to a rectangular portion using any of the manners used to distribute a greater amount of the biologically active material to the end sections (see section 5.3, supra).

6. Barrier Layer Over the Middle Section

In yet another embodiment, there is a barrier layer placed over the middle section of the outer surface, so that the end sections of the outer surface are allowed to release greater amounts of the biologically active material relative to the middle section. The middle and end sections are covered with a coating composition containing biologically active material. A covering or barrier layer is then placed over the middle section to limit the release of the biologically active material. In this way, the release ratio of biologically active material from the end sections is relatively greater than from the middle section.

Examples of such barrier layers include, but not limited to, a top-coating layer covering the middle section. When the medical device of the present invention is a stent, examples of such barrier layers include, but not limited to, a sheath with or without apertures or openings. Suitable material for making such barrier layer include, but not limited to, hydrophobic polymers listed in section 2.2, supra.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A medical device for delivering a biologically active material to a body tissue of a patient in need of treatment, wherein the medical device comprises a tubular portion comprising an outer surface; a plurality of struts that form a plurality of openings; a plurality of non-structural elements integral with and projecting from the struts into the openings, wherein the non-structural elements are distributed throughout the outer surface; and a coating comprising a biologically active material disposed on the struts and the non-structural elements.

2. The medical device of claim 1, wherein the non-structural elements are configured in a shape selected from the group consisting of a cone, a truncated cone, an oval, a straight rod, a bent rod, and a rod having heads at the ends.

3. The medical device of claim 1, wherein the non-structural elements are configured in a shape selected from the groups consisting of hoops, knots and bends.

4. The medical device of claim 1, which comprises a tubular portion comprising an outer surface, wherein the non-structural elements are located in a radially asymmetric distribution on the outer surface.

5. The medical device of claim 4, wherein the non-structural elements are distributed in a rectangular portion of the outer surface.

6. The medical device of claim 5, wherein the rectangular portion is parallel to longitudinal axis of the tubular portion.

7. The medical device of claim 6, wherein the rectangular portion and the tubular portion have same length.

8. The medical device of claim 7, wherein the surface area of the rectangular portion is from about 25% to about 75% of the entire surface area of the outer surface.

9. The medical device of claim 1, which comprises a tubular portion comprising an outer surface, wherein the outer surface has a middle section and end sections, and wherein the end sections comprise a greater number of the non-structural elements per unit length of the outer surface than the middle section.

10. The medical device of claim 1, wherein the biologically active material is selected from the group consisting of paclitaxel, actinomycin, sirolimus, tacrolimus, everolimus, dexamethasone, halofuginone and hydrophobic nitric oxide adducts.

11. The medical device of claim 1, the medical device is a stent.

12. A medical device for delivering a biologically active material to a body tissue of a patient in need of treatment, wherein the medical device comprises a plurality of struts that form a plurality of openings; a plurality of non-structural elements integral with and projecting from the struts into the openings; and a coating comprising a biologically active material disposed on the struts and the non-structural elements, wherein the biologically active material is selected from the group consisting of paclitaxel, actinomycin, sirolimus, tacrolimus, everolimus, dexamethasone, halofuginone and hydrophobic nitric oxide adducts.

13. The medical device of claim 12, wherein the non-structural elements are configured in a shape selected from the group consisting of a cone, a truncated cone, an oval, a straight rod, a bent rod, and a rod having heads at the ends.

14. The medical device of claim 12, wherein the non-structural elements are configured in a shape selected from the groups consisting of hoops, knots and bends.

15. The medical device of claim 12, wherein the medical device is a stent.

* * * * *